United States Patent [19]

Draeger et al.

[11] Patent Number: 4,457,936
[45] Date of Patent: Jul. 3, 1984

[54] USE OF HYDROXYPHENYL-THIAZOLE-, -THIAZOLINE- AND -THIAZOLIDINE-CARBOXYLIC ACIDS, FOR INFLUENCING THE COLLAGEN METABOLISM

[75] Inventors: Eberhard Draeger, Frankfurt am Main; Henning Lubbers, Schwalbach, both of Fed. Rep. of Germany

[73] Assignee: Hoechst Aktiengesellschaft, Frankfurt am Main, Fed. Rep. of Germany

[21] Appl. No.: 366,318

[22] Filed: Apr. 7, 1982

Related U.S. Application Data

[63] Continuation of Ser. No. 228,975, Jan. 27, 1981, abandoned.

[30] Foreign Application Priority Data

Jan. 29, 1980 [DE] Fed. Rep. of Germany ....... 3002989

[51] Int. Cl.$^3$ .................. A61K 31/425; C07D 277/62
[52] U.S. Cl. ..................................... 424/270; 548/200; 548/201
[58] Field of Search ................. 548/201, 200; 424/270

[56] References Cited

U.S. PATENT DOCUMENTS

| | | | |
|---|---|---|---|
| 3,809,754 | 5/1974 | Bertrand | 424/270 |
| 3,882,110 | 5/1975 | Clemence et al. | 260/247.1 M |
| 4,367,233 | 1/1983 | Clark et al. | 424/270 |

FOREIGN PATENT DOCUMENTS

| | | |
|---|---|---|
| 2245560 | 3/1974 | Fed. Rep. of Germany . |
| 3002989 | 1/1980 | Fed. Rep. of Germany . |
| 2062120 | 6/1971 | France . |
| 2247243 | 5/1975 | France . |
| 1584981 | 1/1947 | United Kingdom . |
| 1292170 | 10/1972 | United Kingdom . |
| 1382887 | 2/1975 | United Kingdom . |

OTHER PUBLICATIONS

Huntress et al., J. Am. Chem. Soc. 65, 2167–2169 (1943).
Chem. Abstr. 87, 117845s (1977).
Basic Principles of Org. Chem., Roberts et al. W. A. Benjamin, Inc., New York (1965) pp. 1118–1119.
JACS vol. 70, 1667–1668 (1948).

Primary Examiner—Nicholas S. Rizzo
Attorney, Agent, or Firm—Curtis, Morris & Safford

[57] ABSTRACT

What are disclosed are hydroxyphenyl-thiazole-, -thiazoline- and -thiazolidine-carboxylic acids of the formulae

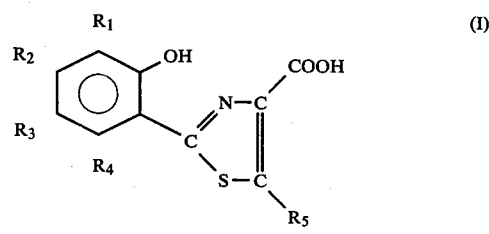

and

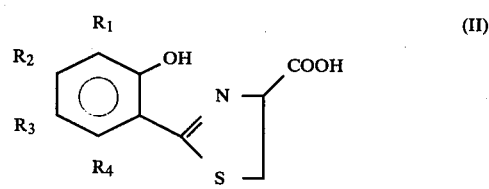

in which
$R_1$ and $R_3$, independently from each other, are hydrogen, methyl, chlorine or bromine, and $R_1$ and $R_3$ may alternatively be nitro, amino or sulfonylamido;
$R_2$ is hydrogen, hydroxyl or methyl;
$R_4$ is hydrogen or methyl; and
$R_5$ is hydrogen, methyl, phenyl or —COOH;
and their salts with physiologically acceptable bases, a process for the preparation thereof and their use for influencing the collagen metabolism.

4 Claims, No Drawings

USE OF HYDROXYPHENYL-THIAZOLE-, -THIAZOLINE- AND -THIAZOLIDINE-CARBOXYLIC ACIDS, FOR INFLUENCING THE COLLAGEN METABOLISM

This is a continuation, of application Ser. No. 228,975, filed Jan. 27, 1981, now abandoned.

In a number of diseases (for example scleroderma, keloid formation, hypertrophic cicatrices, diabetes, hepatocirrhosis, arteriosclerosis), collagen is synthetized in anomalous amounts and deposited in the extracellular space. This collagen overproduction is very often directly responsible for the serious consequences of the disease, so that reduction of the deposited collagen amounts has a positive influence on the course of the disease. It is known that treatment of the diseases involving excess collagen synthesis is attempted by means of most different medicaments.

As an example, the pharmacotherapy of scleroderma may be cited. According to G. Herbai, B. Blom, H. Boström, Acta Med. Scand. 201, 203–206 (1977), the following substances or groups thereof are or were used for the therapy of human beings:
D-thyroxine
Hydralazine
Adrenal cortiocosteroids (Prednisolon)
D-penicillamine (Cuprimine$^{(R)}$)
Stillbestrol derivatives (Anti-estrogens), Cyclofenil
low molecular dextran (Theomakrodex)
Immunosupressives (Azathioprin, Imurel $^{(R)}$)
Chlorambucil (Leukeran $^{(R)}$)
Benzyl-penicillin-diethylamino-ethyl ester
Gestagen hormone Norethisterone (Primolut-Nor $^{(R)}$)
Hydroxyprogesterone-capronate (Proluton-depo $^{(R)}$)
Potassium-p-aminobenzoate, salicylates, dimethyl sulfoxide,
EDTA
Phenoxybenzamine (dibenzyline), dipyridamol (Persantin)
Nicotic acid-procaine However, a satisfactory therapy using these medicaments was possible either not at all or to a limited extent only, because the corresponding activity principle often permitted only a mere symptomatic influence on secondary disturbances caused indirectly by the excess collagen deposits, or, as in the case of the substances comprising hormones, a too radical alteration of the metabolism was the result. Other substances, such as penicillamine, due to their interference with other metabolic processes, proved to have side effects to such an extent that they are unfit for long-term therapy.

A very selective inhibition of collagen biosynthesis can be obtained by influencing the collagen-specific hydroxylation reaction in the course of which protein-bound proline or lysine is hydroxylated by the enzymes proline and lysine hydroxylase, respectively. When this reaction is suppressed by inhibitors, a nonfunctioning, insufficiently hydroxylated collagen molecule is formed which can be released from the cell into the extracellular space in only small amounts. Furthermore, the insufficiently hydroxylated collagen cannot be incorporated into the collagen matrix and is easily degraded proteolytically. As a consequence of these effects, the total amount of collagen deposited in the extracellular space is decreased.

Inhibitors of prolin and lysine hydroxylase are the subject of the present invention.

It has been found that compounds of the formulae

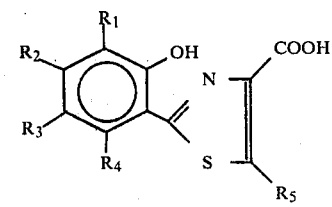

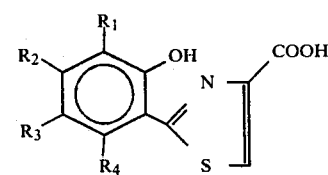

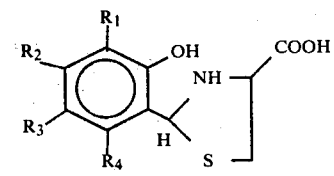

in which
$R_1$ and $R_3$, independently of each other, are hydrogen, methyl, chlorine or bromine, and $R_1$ or $R_3$ may alternatively be nitro, amino or sulfonylamido;
$R_2$ is hydrogen, hydroxyl or methyl;
$R_4$ is hydrogen or methyl; and
$R_5$ is hydrogen, methyl, phenyl or —COOH;
and their salts with physiologically acceptable bases are selectively acting inhibitors of collagen biosynthesis.

Preferred compounds of the formulae I through III are
2-(5-methyl-2-hydroxy-phenyl)thiazole-4-carboxylic acid sodium
2-(5-chloro-2-hydroxy-phenyl)thiazole-4-carboxylic acid sodium
2-(5-methyl-2-hydroxy-phenyl-)5-phenyl-thiazole-4-carboxylic acid sodium
2-(2,4-dihydroxy-phenyl-)5-phenyl-thiazole-4-carboxylic acid sodium
2-(5-methyl-2-hydroxy-phenyl-)thiazole-4,5-dicarboxylic acid sodium
2-(2-hydroxy-phenyl-)thiazoline-4-carboxylic acid sodium
2-(5-chloro-2-hydroxy-phenyl-)-thiazoline-4-carboxylic acid sodium
2-(2,4-dihydroxy-phenyl-)thiazoline-4-carboxylic acid sodium
2-(2-hydroxy-phenyl-)thiazolidine-4-carboxylic acid
2-(3,5-dichloro-2-hydroxy-phenyl-)thiazolidine-4-carboxylic acid
2-(5-nitro-2-hydroxy-phenyl-)thiazolidine-4-carboxylic acid For salt formation, potassium, calcium or ammonia may alternatively be used instead of sodium.

The carboxylic acids of the formula I can be prepared according to known methods (Elderfield, Heterocyclic Compounds, vol. 5, p. 624) from salicylic acid thioamides by reaction with alpha-halocarbonyl compounds according to the following scheme:

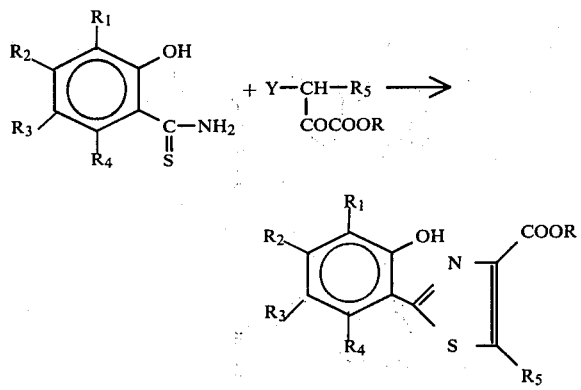

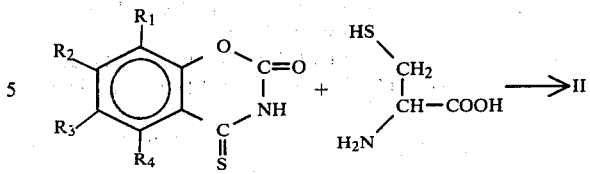

in which $R_1$ through $R_4$ are as defined above, Y is chlorine or bromine, R is hydrogen or alkyl, preferably having from 1 to 4 carbon atoms, $R_5$ may be hydrogen, methyl, phenyl, or —COOR. In the case where R is alkyl, the esters can be hydrolyzed, preferably in an alkaline medium, to yield I.

As alpha-halocarbonyl compounds, for example bromopyruvic acid or the esters thereof, phenyl-bromopyruvic acid or the esters thereof, chloro- or bromo-oxaloacetic acid ester, or 3-bromo-2-oxo-butyric acid or the esters thereof are used.

Preferred thioamides are salicylic acid thioamide, 5-methyl-2-hydroxy-thiobenzamide or 2,4-dihydroxy-thiobenzamide.

The carboxylic acids of the formula II, too, are obtained according to methods known from the literature (Elderfield, loc. cit., p. 681). Thioamides and iminoethers react with cysteine or its derivatives to yield thiazoline-4-carboxylic acid or the derivatives thereof.

This process can be applied also to salicylic acid thioamides.

An especially smooth course of the reaction is ensured in accordance with the invention by using the O,N-carbonyl compounds of salicylic acid thioamides, the 2-oxo-4-thiono-dihydro-1,3-benzoxazines, according to the following scheme:

The benzoxazine derivatives serving as starting material are obtained according to methods known from literature [Pharmazie 21 (3), 161 (1966)] from salicylic acid thioamides. Preferred thioamides are the same as indicated above.

In addition to cysteine (D- or L-form or racemate) or its salts such as the hydrochloride, the esters of cysteine may also be used as reactants.

The carboxylic acids of the formula III are easily obtainable from salicylic aldehyde or its derivatives by condensation with cysteine according to the following scheme. Literature references on the condensation of carbonyl compounds with cysteine can be taken from Elderfield, loc. cit., p.698.

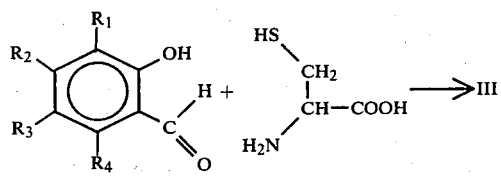

Preferred aldehydes are: salicylic, 3,5-dichlorosalicylic, 3,5-dibromosalicylic or 5-nitrosalicylic aldehyde.

The inhibiting effect of the substances in accordance with the invention on collagen biosynthesis can be examined in an enzyme test analogous to the method of B. Peterkofsky and R. DiBlasio [Anal. Biochem. 66, 279–286 (1975)]. In this test, insufficiently hydroxylated collagen is enzymatically hydroxylated in the presence of molecular oxygen, iron-II ions, alpha-ketoglutaric and ascorbic acid.

As enzymes, prolyl hydroxylase or lysyl hydroxylase can be used and applied in a cell-free medium. The effect of the substances of the invention can be measured furthermore in cell and tissue cultures.

The inhibiting effect ($DI_{50}$) is that concentration at which the enzyme reaction is inhibited by 50%. The $DI_{50}$ data of some of the compounds of the invention are listed in the following Table.

TABLE

| Substance | $DI_{50}$ propyl-hydroxylase (μM) | $DI_{50}$ lysylhydroxy-lase (μM) | $DI_{50}$ cell culture (μM) |
|---|---|---|---|
| [5-methyl benzothiazoline COONa structure] | 28 | 28 | 34 |
| [benzothiazoline COONa structure] | 20 | 28 | |

TABLE-continued
| Structure | | |
|---|---|---|
| 4-Cl, 2-OH phenyl, N=C(COONa)-S (thiazoline) | 16 | 12 17 |
| 4-HO, 2-OH phenyl, N=C(COONa)-S | 26 | 16 |
| 2-OH phenyl, NH-CH(COOH)-S | 28 | 28 |
| 4-O₂N, 2-OH phenyl, NH-CH(COOH)-S | 50–100 | 50–100 |
| 3,5-diBr, 2-OH phenyl, NH-CH(COOH)-S | 50–100 | 10 |
| 3,5-diCl, 2-OH phenyl, NH-CH(COOH)-S | 50–100 | 50–100 |
| 4-CH₃, 2-OH phenyl, N=C(COONa)-S (thiazoline) | 42 | 67 |
| | DI₅₀ μM | |
|---|---|---|
| | (L) | (P) |
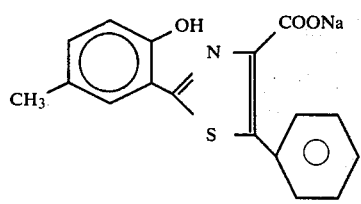
34   26
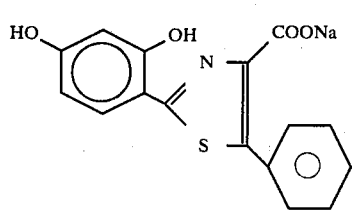
21   27

TABLE-continued

| Structure | | |
|---|---|---|
| 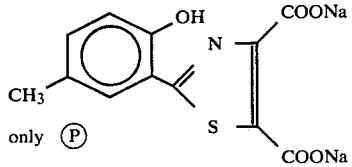 only Ⓟ | 144 | 67 |
| 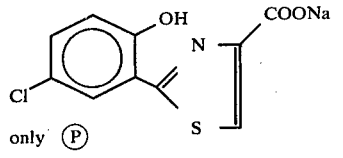 only Ⓟ | 188 | 71 |
| 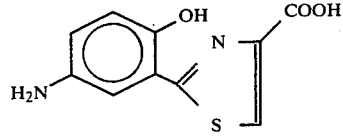 × HCl | 29 | 5.6 |
| 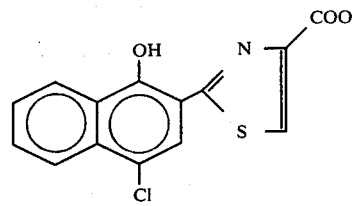 | 31.6 | 28.2 |

The following examples illustrate the invention.

EXAMPLE 1

7 g of phenylbromopyruvic acid, dissolved in 20 ml of glacial acetic acid, are added to a solution having a temperature of 60° C. of 5 g of 5-methyl-2-hydroxy-thiobenzamide in 30 ml of glacial acetic acid. The reaction product precipitates immediately. It is diluted with 25 ml of water, boiled and clarified in a hot state. From the filtrate, 7.5 g (84%) 2-(5-methyl-2-hydroxyphenyl)-5-phenylthiazole-4-carboxylic acid having a melting point of 193°–194° C. crystallize. By dissolving the compound in the calculated amount of soda solution, the sodium salt of this compound is obtained.

EXAMPLE 2

According to Example 1, 2-(2,4-dihydroxyphenyl)-5-phenylthiazole-4-carboxylic acid having a melting point of 335°–340° C. is obtained from phenylbromopyruvic acid and 2,4-dihydroxy-thiobenzamide. By dissolving the compound in Na₂CO₃ solution and adding sodium chloride, the sodium salt is obtained.

EXAMPLE 3

By the condensation of molar amounts of 5-methyl-2-hydroxy-thiobenzamide and chloro-oxaloacetic acid ethyl ester, 2-(5-methyl-2-hydroxyphenyl)-thiazole-4,5-dicarboxylic acid ethyl ester having a melting point of 80°–81° C. is obtained. When this ester is boiled in alcoholic sodium hydroxide solution, the disodium salt of 2-(5-methyl-2-hydroxyphenyl)-thiazole-4,5-dicarboxylic acid is directly obtained (melting point of the acid: 264°–266° C.).

EXAMPLE 4

20 g of pyruvic acid are brominated in 30 ml of water with 35 g of bromine at 70°–80° C. 28 g of 5-chloro-2-hydroxy-thiobenzamide are added at 20° C. to the solution of bromopyruvic acid obtained. The temperature rises to 45° C., and the reaction product crystallizes slowly. It is cooled, diluted with 100 ml of ethanol, suction-filtered and yields after drying 21 g of 2-(5-chloro-2-hydroxyphenyl)-thiazole-4-carboxylic acid having a melting point of 292°–294° C. By dissolving the compound in warm soda solution, the sodium salt is obtained on cooling.

EXAMPLE 5

According to Example 4, 2-(5-methyl-2-hydroxyphenyl)-thiazole-4-carboxylic acid having a melting point of 273°–274° C. is obtained from 5-methyl-2-hydroxyphenylthiobenzamide and bromopyruvic acid.

EXAMPLE 6

40 g of cysteine hydrochloride are dissolved in 150 ml of oxygen-free water, 40 g of 6-methyl-2-oxo-4-thionedihydro-1,3-benzoxazine (prepared according to Einhorn and Mettler, B 35, 350, (1902) from 5-methyl-2-hydroxythiobenzoic acid amide) are added, and subsequently, 7.5 ml of 33% NaOH are added dropwise while slowly passing nitrogen through the batch, which is then heated to 80°–90° C. Further 12.5 ml of concentrated NaOH are added dropwise within 3 hours. After a further 3 hours, 50 g of sodium chloride are added, and the product is allowed to crystallize while cooling. After recrystallization from a small amount of water, 35 g of 2-(5-methyl-2-hydroxyphenyl)-thiazoline-4-carboxylic acid sodium are obtained. The free carboxylic acid has a melting point of 255° C.

In the same manner, the following thiazoline derivatives are obtained:

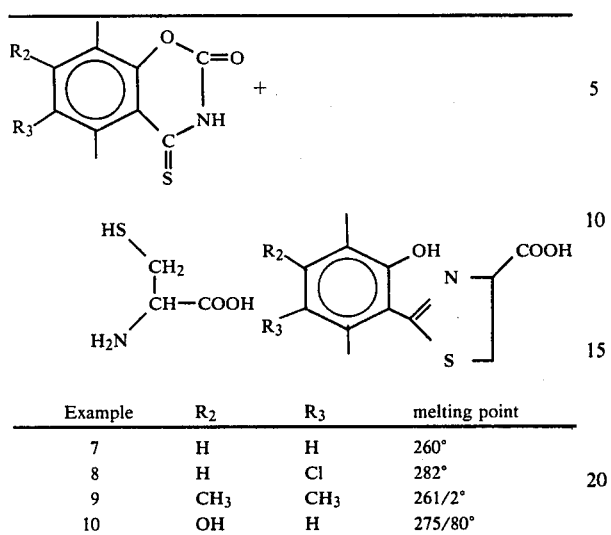

| Example | R₂ | R₃ | melting point |
|---------|------|------|---------------|
| 7 | H | H | 260° |
| 8 | H | Cl | 282° |
| 9 | CH₃ | CH₃ | 261/2° |
| 10 | OH | H | 275/80° |

EXAMPLE 11

20 g of L(+) cysteine hydrochloride are dissolved in 150 ml of water, 12 g of potassium acetate and subsequently 100 ml of ethanol are added. The batch is mixed with a solution of 17 g of salicylic aldehyde in 50 ml of ethanol. The temperature rises to 35° C. and the reaction product crystallizes after a short time. 19 g of 2-(2-hydroxyphenyl)-thiazolidine-4-carboxylic acid having a melting point of 169° C. and a $\alpha_D^{24}$ of −44.5° C. are obtained.

In the same manner, the following thiazolidines are obtained:

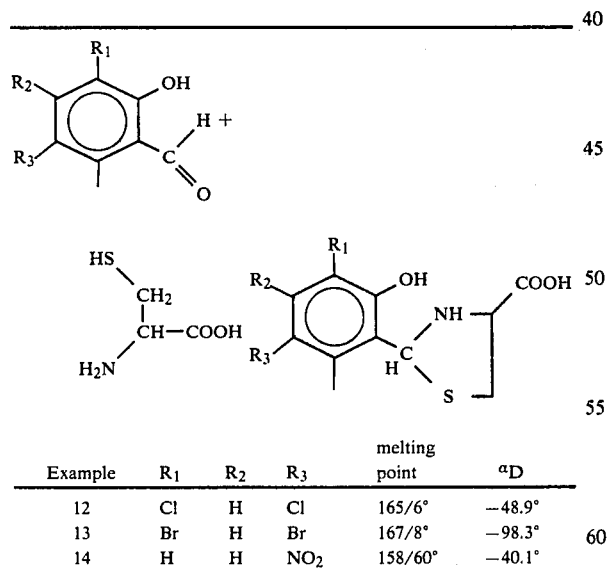

| Example | R₁ | R₂ | R₃ | melting point | $\alpha_D$ |
|---------|------|------|------|---------------|------------|
| 12 | Cl | H | Cl | 165/6° | −48.9° |
| 13 | Br | H | Br | 167/8° | −98.3° |
| 14 | H | H | NO₂ | 158/60° | −40.1° |

What is claimed is:

1. A pharmaceutical preparation for inhibiting collagen biosynthesis which comprises an effective inhibiting amount of a carboxylic acid selected from the group of acids having the formulas

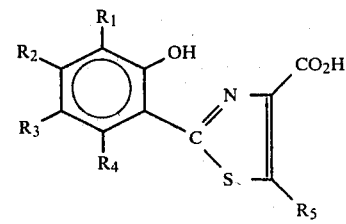

and

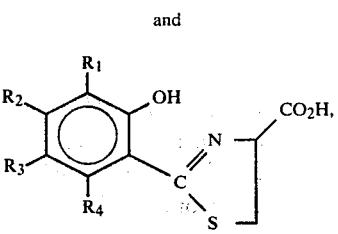

or a soluble, physiologically acceptable carboxylate salt of such an acid, formed with a base, wherein $R_1$ and $R_3$ independently of each other are hydrogen, methyl, chlorine, or bromine, or one of $R_1$ or $R_3$ is hydrogen, methyl, chlorine, or bromine and the other is nitro, amino, or sulfonylamido;

$R_2$ is hydrogen, hydroxyl, or methyl;

$R_4$ is hydrogen or methyl, but not all of $R_1$–$R_4$ are hydrogen; and $R_5$ is hydrogen, methyl, phenyl, or carboxyl, together with a pharmaceutically acceptable carrier therefor.

2. A method for inhibiting collagen biosynthesis in a patient requiring such treatment, which method comprises administering to said patient an effective inhibiting amount of a carboxylic acid selected from the group of acids having the formulas

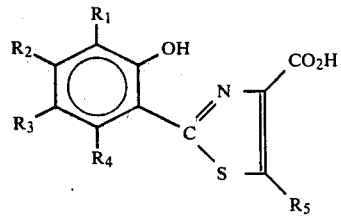

and

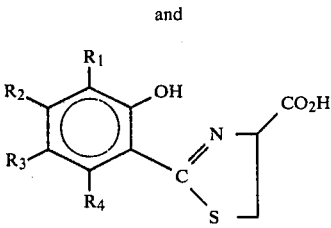

or a soluble, physiologically acceptable carboxylate salt of such an acid, formed with a base, wherein $R_1$ and $R_3$ independently of each other are hydrogen, methyl, chlorine, or bromine, or one of $R_1$ or $R_3$ is hydrogen, methyl, chlorine, or bromine and the other is nitro, amino, or sulfonylamido;

$R_2$ is hydrogen, hydroxyl, or methyl;

$R_4$ is hydrogen or methyl, but not all of $R_1$–$R_4$ are hydrogen; and $R_5$ is hydrogen, methyl, phenyl, or carboxyl.

3. A pharmaceutical preparation for inhibiting collagen biosynthesis which comprises an effective inhibiting amount of a carboxylic acid of the formula $$\text{(III)}$$

or of a soluble, physiologically acceptable, carboxylate salt of such an acid formed with a base, wherein
$R_1$, $R_3$, and $R_4$ are, independently of each other, hydrogen, methyl, chlorine, or bromine, or one of $R_1$ or $R_3$ is hydrogen, methyl, chlorine, or bromine and the other is nitro; and
$R_2$ is hydrogen, methyl, or hydroxyl; together with a pharmaceutically acceptable carrier therefor.

4. A method for inhibiting collagen biosynthesis in a patient requiring such treatment, which method comprises administering to said patient an effective inhibiting amount of a carboxylic acid of the formula $$\text{(III)}$$

or of a soluble, physiologically acceptable, carboxylate salt of such an acid formed with a base, wherein
$R_1$, $R_3$, and $R_4$ are, independently of each other, hydrogen, methyl, chlorine, or bromine, or one of $R_1$ or $R_3$ is hydrogen, methyl, chlorine, or bromine and the other is nitro; and
$R_2$ is hydrogen, methyl, or hydroxyl.

* * * * *